United States Patent [19]

Mahgerefteh et al.

[11] Patent Number: 5,570,082

[45] Date of Patent: Oct. 29, 1996

[54] REMOTE WETNESS SENSOR FOR DIAPERS

[76] Inventors: Nasser Mahgerefteh, 21101 Shaw La., Huntington Beach, Calif. 92646; Israel D. Schleicher, 10901 Bahia Ct., Bakersfield, Calif. 93311

[21] Appl. No.: 542,723

[22] Filed: Oct. 13, 1995

[51] Int. Cl.$^6$ ................................................ G08B 21/00
[52] U.S. Cl. ............................... 340/604; 604/361
[58] Field of Search ........................... 340/573, 604, 340/539; 604/358, 361; 73/73

[56] References Cited

U.S. PATENT DOCUMENTS

| | | | |
|---|---|---|---|
| 3,460,123 | 8/1969 | Bass | 340/235 |
| 3,707,711 | 10/1972 | Cole et al. | 340/280 |
| 3,818,468 | 6/1974 | Toth et al. | 340/224 |
| 4,471,344 | 9/1984 | Williams | 340/572 |
| 4,539,559 | 9/1985 | Kelly et al. | 340/573 |
| 4,754,264 | 6/1988 | Okada et al. | 340/604 |
| 5,025,247 | 6/1991 | Banks | 340/539 |
| 5,047,750 | 9/1991 | Hector | 340/573 |
| 5,121,630 | 6/1992 | Calvin | 340/604 |
| 5,392,032 | 2/1995 | Kline et al. | 340/604 |
| 5,463,377 | 10/1995 | Kronberg | 340/605 |

*Primary Examiner*—Jeffery Hofsass
*Assistant Examiner*—Timothy Edwards, Jr.

[57] ABSTRACT

A system for detecting wetness in diapers for the propose of calling the attention of a caretaker. The system is based on the nonlinear interaction of an implanted device inside the diaper with a low distortion background electromagnetic field. The background field is generated by a transmitter external to the diaper. The device is a combination of an antenna, a nonlinear element and two electrodes. Upon a wet condition the resistance between the two electrodes decrease, resulting in an increase in coupling between the antenna and the nonlinear element. The ensuing nonlinear interaction between the antenna and the background field gives rise to harmonics of the field which are detected by a receiver. The receiver which is also external to the diaper triggers a suitable alarm.

9 Claims, 1 Drawing Sheet

REMOTE WETNESS SENSOR FOR DIAPERS

FIELD OF INVENTION

This invention relates to the field of sanitary undergarments, in particular to undergarments with wetness indicators.

BACKGROUND AND PRIOR ART

A sensor for wetness condition of diapers is of great benefit to a caretaker of a baby as it relieves the caretaker from the frequent task of checking on the baby. It is of great benefit to the baby as the immediate attention of the caretaker prevents the condition known as "diaper rash". A sensor that remotely calls the attention of the caretaker is of obvious added benefit. Wetness sensors with remote alarm have been suggested by several authors. For example, Kline et al. in U.S. Pat. No. 5,392,032 uses a pair of electrodes as sensors and a detachable electronic circuit to power an alarm. It will be prohibitively expensive to implant the electronic circuit in a disposable diaper. Since disposable diapers are preferred by many, an implantable sensor of low cost has an advantage over that described in the above Patent for two main reasons: 1) a detachable unit must be large (large enough so it cannot be swallowed by the baby in case it detaches or left near the baby by neglect)—a large attachment will cause discomfort and 2) caretakers would not like to handle a soiled diaper for the purpose of detaching the reusable unit.

The present invention provides a cost effective remote wetness sensor for disposable diapers. The invention borrows an idea from theft prevention systems that utilize the so called Passive Tag. Such a system is described by Cole et. al in U.S. Pat. No. 3,707,711. A tag, or in the present invention an implant in the diaper interferes with the transmission of an external transmitter only upon a condition of wet diaper. This interference is detected by a receiver also external to the diaper. Since with early detection of wetness the amount of absorbent filler in the diaper can be reduced, it is possible that with the present invention the total cost, over time, will actually be lower.

DESCRIPTION OF THE PREFERRED EMBODIMENT

Figure 1:
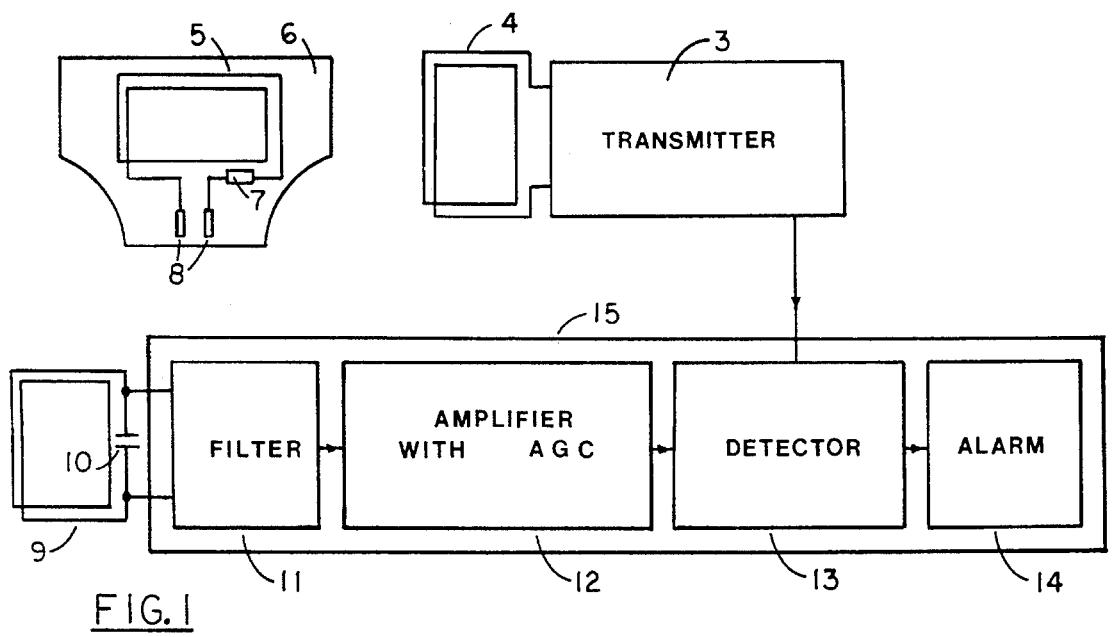

The following figures depict the preferred embodiment of the invention:

FIG. 1 General block diagram.

Figure 2:
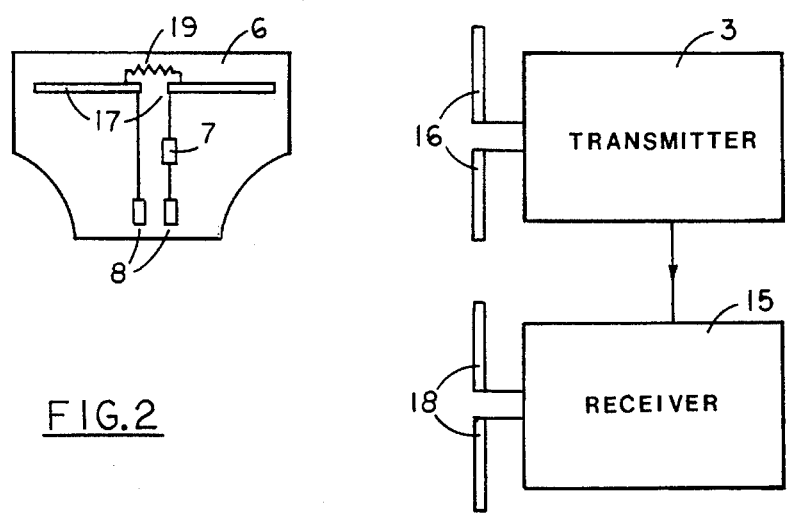

FIG. 2 Alternative mode of operation.

With reference to FIG. 1, a transmitter 3 drives a low distortion sinusoidal electric current into coil antenna 4. The frequency of the current waveform is in the range of 100 KHz to 250 KHz. Consequently a magnetic field is generated which induces a sinusoidal electric voltage in coil 5. Coil 5 is implanted in diaper 6 together with a series connection of a nonlinear element 7 and a set of two electrodes 8. Coil 5 is made of a few turns of thin magnet wire and has as large as possible aperture that can fit inside the lining of the diaper. The nonlinear element 7 is preferably a semiconductor diode. Electrodes 8 are located in the section of the diaper most likely to become wet. When the diaper is wet, the resistance between electrodes 8 is reduced and thus a better coupling between the nonlinear element 7 and coil 5 is created. The induced voltage in coil 5 causes current to flow in the nonlinear element 7. Because of the nonlinearity, harmonics of the induction frequency are generated. Thus, upon wet condition, the magnetic field in the surrounding of the diaper is modified to include harmonics of the transmitted frequency. These harmonics, preferably the second harmonic which is generally larger in magnitude, is detectable by an antenna comprised of coil 9 and capacitor 10 and a receiver 15 comprised of the blocks shown in FIG. 1. Coil 9 and capacitor 10 are tuned to resonate at the second harmonic frequency. If the transmitter frequency is 250 KHz, the resonant frequency is 500 KHz—still under the range of Am radio, thus avoiding interference from radio stations. Since the received energy at the harmonic frequency is very low, more selectivity and amplification is needed: this is provided by filter 11 and amplifier 12. Since the orientation of coil 5 is random, a null condition is possible. In a null condition, no voltage is induced in coil 5 and no wetness detection is possible. Since exact null is rare and since the baby is likely to move, it does not create a major drawback. However it is clear that the signal level at the receiver 15 varies widely. For that reason amplifier 12 is equipped with an automatic gain control (AGC) which sets the gain to provide a constant level at the input of detector 13. Detector 13 is only responsive to signal of the desired harmonic of the transmitted frequency, 500 KHz for example. Upon detection of harmonic frequency the detector triggers the alarm circuit 14.

SUMMARY AND RAMIFICATIONS

The invention described above works well in a limited range; for example when monitoring a baby in a crib. A longer range is desired when, for example, it is needed to monitor a toddler in a room. A longer range can be achieved by either one or more of the following: 1) Increasing the operating frequency. 2) Adding turns and/or adding a ferromagnetic core to coil 5. 3) Increasing the transmitted power. 4) Increasing the coupling between coil 5 and nonlinear element 7.

The advantage of the preferred lower operating frequency is in that that it is less likely to interfere with radio and other sensitive equipment and less likely to be disturbed by such equipment. In case the nonlinear element is a semiconductor diode, a bias DC current, if initiated upon a wet condition, will greatly improve the coupling and hence the sensitivity. The simplest way to initiate the desired DC current is to make electrodes 8 of two different conductive materials with different electrochemical potentials. A similar idea is described by Kline et al. in the Patent mentioned earlier in this disclosure. Connected in the correct polarity relative to the nonlinear element (a semiconductor diode) 7, the two electrodes 8 together with the baby's urine will form a battery that will initiate a DC current as well as provide the necessary coupling to coil 5.

Although a common PN junction diode is a preferred choice for element 7, other choices are possible: a back-diode, a varactor diode, a varistor, a nonlinear ferroelectric device or a nonlinear ferromagnetic device.

As depicted in FIG. 1, the preferred embodiment generates and detects magnetic fields. An embodiment in which an electric field is generated and detected is depicted in FIG. 2. The only difference between the two methods is the type of antennas used: electric dipoles 16,17 and 18, rather than coils. Resistor 19 (or an inductor) is added to provide a closed circuit if a DC bias is employed as described above.

Transmitter 3, receiver 15 and associated antennas can be packaged in the same enclosure together with a battery that provides the necessary power. Since the transmitter requires substantial power, an intermittent mode of operation is suggested. In this mode, the transmitter is switched on periodically every few minutes and operates for a very short duration—just long enough for detecting a set condition.

FIG. 1 and FIG. 2 show a connection between the transmitter and the detector block of the receiver. This connection is required for the purpose of accomplishing the detection since the detector compares the harmonic frequency to the transmitted frequency and triggers the alarm only if the harmonic is an exact multiple of the transmitted frequency. There are few possible detection schemes: 1) A coherent detector, uses a balanced mixer and provides a DC output only when the detected signal is a harmonic of the transmitted signal. 2) A digital frequency analyzer, performs a fourier transform on time samples of a combines signal of the transmitter and the received signal. 3) By modifying the transmitter to generate a modulated field having a narrow bandwidth, the detector can be designed to identify the specific modulation scheme. This method does not require a connection between the transmitter and the detector.

What we claim as a new invention:

1. A device which is included in the lining of a diaper, that upon a set condition in the diaper generates harmonic frequencies of a background electromagnetic field produced by a remotely located transmitter, the harmonic frequency detectable by a remotely located receiver which also activates an alarm to call the attention of a caretaker, the device comprises:

an antenna coupled to a nonlinear electrical device via a set of two parallel electrodes, said electrodes embedded in the lining of the diaper in an area likely to experience wetness and adapted to provide substantially stronger coupling between said antenna and said nonlinear device when subjected to wetness.

2. The invention of claim 1 wherein said transmitter generates a modulated narrow band electromagnetic field and said receiver is tuned to a selected harmonic of said field and capable of discriminating between said harmonic and an interfering signal based on the character of said modulation.

3. The device of claim 1 wherein said electromagnetic field has a predominate magnetic component, said nonlinear element has two terminals and said antenna is a coil having at least one turn of thin electrical conductor, said conductor having two ends, first end of said conductor connected to first terminal of said nonlinear element, second terminal of said nonlinear element connected to first of said electrodes, second of said electrodes connected to second end of said conductor.

4. The device of claim 3 wherein said antenna includes a ferromagnetic core.

5. The invention of claim 3 wherein said nonlinear element is a semiconductor diode and said electrodes are made of two different materials chosen to develop different electrochemical potentials when immersed in urine for the purpose of initiating a flow of electrical direct current through said nonlinear element, said current providing a bias to said nonlinear element thus increasing the level of said generated harmonics upon wet condition.

6. The device of claim 1 wherein said electromagnetic field has a predominate electric component, said nonlinear element has two terminals and said antenna is a dipole made of two essentially collinear conductors, said conductors having essentially the same length, first of said conductors connected to first terminal of said nonlinear element, second terminal of said electrodes connected to first of said electrodes, second of said electrodes connected to second of said conductors.

7. The invention of claim 6 wherein said nonlinear element is a semiconductor diode and said electrodes are made of two different materials chosen to develop different electrochemical potentials when immersed in urine for the purpose of initiating a flow of electrical direct current through said nonlinear element, said invention further including an electrical circuit closing means to enable flow of said direct current, said current providing a bias to said nonlinear element thus increasing the level of said generated harmonics upon a wet condition.

8. The invention of claim 7 wherein said electrical circuit closing means is a resistor.

9. The invention of claim 7 wherein said electrical circuit closing means is an inductor.

* * * * *